(12) United States Patent
Lee et al.

(10) Patent No.: US 8,500,749 B2
(45) Date of Patent: Aug. 6, 2013

(54) APPARATUS AND METHOD FOR INSERTING INTERVERTEBRAL IMPLANTS

(75) Inventors: Randall F. Lee, Arlington, TX (US); Jack E. Zigler, Plano, TX (US); Richard D. Guyer, Plano, TX (US); Michael J. Mojica, Arlington, TX (US)

(73) Assignee: Prescient Surgical Designs, LLC, Grand Prairie, TX (US)

( * ) Notice: Subject to any disclaimer, the term of this patent is extended or adjusted under 35 U.S.C. 154(b) by 154 days.

(21) Appl. No.: 13/089,517

(22) Filed: Apr. 19, 2011

(65) Prior Publication Data

US 2012/0271421 A1 Oct. 25, 2012

(51) Int. Cl.
*A61B 17/70* (2006.01)

(52) U.S. Cl.
USPC .......................................... 606/99; 606/86 A (58) Field of Classification Search
USPC ............................ 606/90, 99, 86 A, 86 B, 279
See application file for complete search history.

(56) References Cited

U.S. PATENT DOCUMENTS

| | | | | |
|---|---|---|---|---|
| 3,486,505 A * | 12/1969 | Morrison | .......................... | 606/90 |
| 5,431,658 A * | 7/1995 | Moskovich | ...................... | 606/99 |
| 6,478,800 B1 * | 11/2002 | Fraser et al. | ...................... | 606/99 |
| 6,599,294 B2 * | 7/2003 | Fuss et al. | ........................ | 606/99 |
| 6,652,533 B2 * | 11/2003 | O'Neil | ............................ | 606/100 |
| 6,755,841 B2 * | 6/2004 | Fraser et al. | ...................... | 606/99 |
| 7,118,580 B1 * | 10/2006 | Beyersdorff et al. | ............ | 606/99 |
| 7,326,250 B2 * | 2/2008 | Beaurain et al. | ............ | 623/17.14 |
| 7,387,635 B2 * | 6/2008 | Keller | .............................. | 606/99 |
| 7,547,309 B2 * | 6/2009 | Bertagnoli et al. | .............. | 606/99 |
| 7,575,576 B2 * | 8/2009 | Zubok et al. | ..................... | 606/90 |
| 7,625,379 B2 * | 12/2009 | Puno et al. | ........................ | 606/99 |
| 7,637,952 B2 * | 12/2009 | Landry et al. | ............... | 623/17.11 |
| 7,722,622 B2 * | 5/2010 | Evans et al. | ...................... | 606/99 |
| 7,749,231 B2 * | 7/2010 | Bonvallet et al. | ................ | 606/99 |
| 7,766,918 B2 * | 8/2010 | Allard et al. | ..................... | 606/90 |
| 7,771,432 B2 * | 8/2010 | Schwab et al. | ................... | 606/99 |
| 7,803,162 B2 * | 9/2010 | Marnay et al. | ................... | 606/99 |
| 7,896,884 B2 * | 3/2011 | Wing et al. | ....................... | 606/90 |
| 7,927,373 B2 * | 4/2011 | Parsons et al. | ............. | 623/17.14 |
| 7,951,154 B2 * | 5/2011 | Schwab et al. | ................... | 606/99 |
| 8,016,829 B2 * | 9/2011 | Mahoney et al. | ........... | 606/86 A |
| 8,038,715 B2 * | 10/2011 | Kim et al. | .................. | 623/17.13 |
| 8,043,344 B2 * | 10/2011 | Evans et al. | ..................... | 606/279 |
| 8,062,304 B2 * | 11/2011 | Blain et al. | ....................... | 606/90 |
| 8,114,088 B2 * | 2/2012 | Miller | ............................. | 606/90 |

(Continued)

OTHER PUBLICATIONS

International Search Report and Written Opinion issued for PCT/US2012/028445, dated Jun. 7, 2012, 9 pages.

*Primary Examiner* — Eduardo C Robert
*Assistant Examiner* — Lynnsy Schneider (57) ABSTRACT

An instrument for inserting an implant between vertebrae includes an upper and a lower ramp each having a respective proximal and a distal end. A bracket assembly is coupled to the upper and lower ramps at the proximal ends. The bracket assembly biases the upper and lower ramps closed at the distal end. A drive member has a longitudinal axis and a screw thread thereon. The drive member is disposed between the upper and lower ramps and extends through a passage in the bracket assembly. An adjustable spreader is operably coupled to the drive member and movable between the upper and lower ramps along the longitudinal axis by rotation of the drive member. The adjustable spreader separates the upper ramp from the lower ramp during forwardly movement along the longitudinal axis. An implant holder is coupled to the adjustable spreader.

30 Claims, 6 Drawing Sheets

U.S. PATENT DOCUMENTS

| | | |
|---|---|---|
| RE43,317 E * | 4/2012 | Fraser et al. .................... 606/99 |
| 2003/0055503 A1 * | 3/2003 | O'Neil ....................... 623/17.11 |
| 2003/0208203 A1 | 11/2003 | Lim et al. |
| 2004/0030387 A1 * | 2/2004 | Landry et al. .............. 623/16.11 |
| 2004/0059271 A1 * | 3/2004 | Berry ............................ 602/32 |
| 2004/0220582 A1 | 11/2004 | Keller et al. |
| 2005/0027300 A1 * | 2/2005 | Hawkins et al. ................ 606/86 |
| 2005/0131407 A1 * | 6/2005 | Sicvol et al. .................... 606/61 |
| 2005/0143747 A1 * | 6/2005 | Zubok et al. .................... 606/90 |
| 2005/0165408 A1 | 7/2005 | Puno et al. |
| 2006/0167461 A1 * | 7/2006 | Hawkins et al. ................ 606/90 |
| 2006/0241641 A1 * | 10/2006 | Albans et al. .................... 606/90 |
| 2007/0016221 A1 * | 1/2007 | Beyersdorff et al. ........... 606/99 |
| 2007/0123903 A1 * | 5/2007 | Raymond et al. ............... 606/99 |
| 2007/0123904 A1 * | 5/2007 | Stad et al. ....................... 606/99 |
| 2007/0185375 A1 * | 8/2007 | Stad et al. ..................... 600/101 |
| 2008/0161817 A1 * | 7/2008 | Parsons et al. .................. 606/90 |
| 2008/0161821 A1 * | 7/2008 | Heinz ............................ 606/99 |
| 2008/0275455 A1 | 11/2008 | Berry et al. |
| 2009/0005784 A1 * | 1/2009 | Blain et al. ...................... 606/90 |
| 2009/0030422 A1 * | 1/2009 | Parsons et al. .................. 606/99 |
| 2009/0048604 A1 * | 2/2009 | Milz et al. ....................... 606/99 |
| 2009/0234362 A1 * | 9/2009 | Blain et al. ...................... 606/90 |
| 2009/0306672 A1 * | 12/2009 | Reindel et al. .................. 606/90 |
| 2010/0069914 A1 * | 3/2010 | Puno et al. ....................... 606/99 |
| 2010/0114183 A1 * | 5/2010 | Wassinger et al. .......... 606/86 A |
| 2010/0160983 A1 * | 6/2010 | Runco et al. ................. 606/86 A |
| 2010/0249792 A1 * | 9/2010 | Bonvallet et al. ............... 606/90 |
| 2010/0262154 A1 * | 10/2010 | Evans et al. ..................... 606/99 |
| 2010/0262199 A1 * | 10/2010 | Wallenstein et al. ....... 606/86 A |
| 2011/0040383 A1 | 2/2011 | Wurfel |
| 2011/0166611 A1 * | 7/2011 | Stinson ....................... 606/86 A |

* cited by examiner

APPARATUS AND METHOD FOR INSERTING INTERVERTEBRAL IMPLANTS

TECHNICAL FIELD

The invention relates to an apparatus and method for inserting intervertebral implants.

BACKGROUND

Intervertebral implants are usually inserted after removal of a damaged disk. The implant is contoured to fit into the interbody space between two adjacent vertebrae. The insertion of the implant between two vertebrae is often challenging. During operation, the adjacent vertebrae are separated by applying sufficient distraction force. The implant is then positioned in the interbody space between the vertebrae.

Existing apparatus for inserting implants in the intervertebral space typically include guide members separated by a spreader. The implant is positioned forwardly of the spreader. The spreader is movable forwardly and rearwardly between the guide members by a drive member. As the spreader is advanced forwardly, the guide members separate the adjacent vertebrae so that the implant may be positioned between the vertebrae. Typically, the implant remains in contact with the guide members as it is advanced forwardly and inserted in the intervertebral space. Thus, the implant is subjected to axial force and shearing.

SUMMARY

An embodiment of the present invention provides an instrument for inserting an implant between vertebrae. The instrument includes an upper and a lower ramp each having a respective proximal and a distal end. The instrument includes a bracket assembly coupled to the upper and lower ramps at the proximal ends. The bracket assembly biases or tilts the upper and lower ramps closed at the distal end. A drive member has a longitudinal axis and a screw thread thereon. The drive member is disposed between the upper and lower ramps and extends through a passage in the bracket assembly.

An adjustable spreader is coupled to the drive member and movable between the upper and lower ramps along the longitudinal axis by rotation of the drive member. The upper ramp bears against the adjustable spreader as the spreader forwardly advances along the longitudinal axis causing the upper ramp to separate from the lower ramp. The extent of separation is defined by the adjustable spreader. An implant holder is coupled to the adjustable spreader. The implant holder is configured to releasably hold the implant during forward advancement along the longitudinal axis. The implant remains separated from the upper and lower ramps during back and forth movement of the implant. The lower ramp remains stationary during back and forth movement of the drive member.

The upper and lower ramps each include a centrally located channel with an aperture near the proximal ends. The adjustable spreader includes a block having a projection sized to move freely within the channel in the lower ramp and an upper surface for supporting the upper ramp. The instrument includes a vertebral stop projecting proximate the distal end of the upper and lower ramps to limit forward advancement of the ramps inside an intervertebral space.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION

Refer now to the drawings, wherein depicted elements are, for the sake of clarity, not necessarily shown to scale and wherein like or similar elements are designated by the same reference numeral through the several views.

Referring to FIGS. 1-4, an instrument 100 for inserting an implant 104 between adjacent vertebrae 108 and 112 in accordance with one embodiment is shown. The instrument 100 has upper and lower ramps 116 and 120, which may be called paddles. The upper and lower ramps 116, 120 have respective proximal and distal ends 124, 126 and 128, 130.

The upper and lower ramps 116 and 120 each include a centrally located channel 118 with an aperture 122 near the proximal ends 124 and 126. The channels 118 originate from the aperture 122 and extend proximate the distal ends 124, 126 of the ramps 116, 120.

Figure 1:
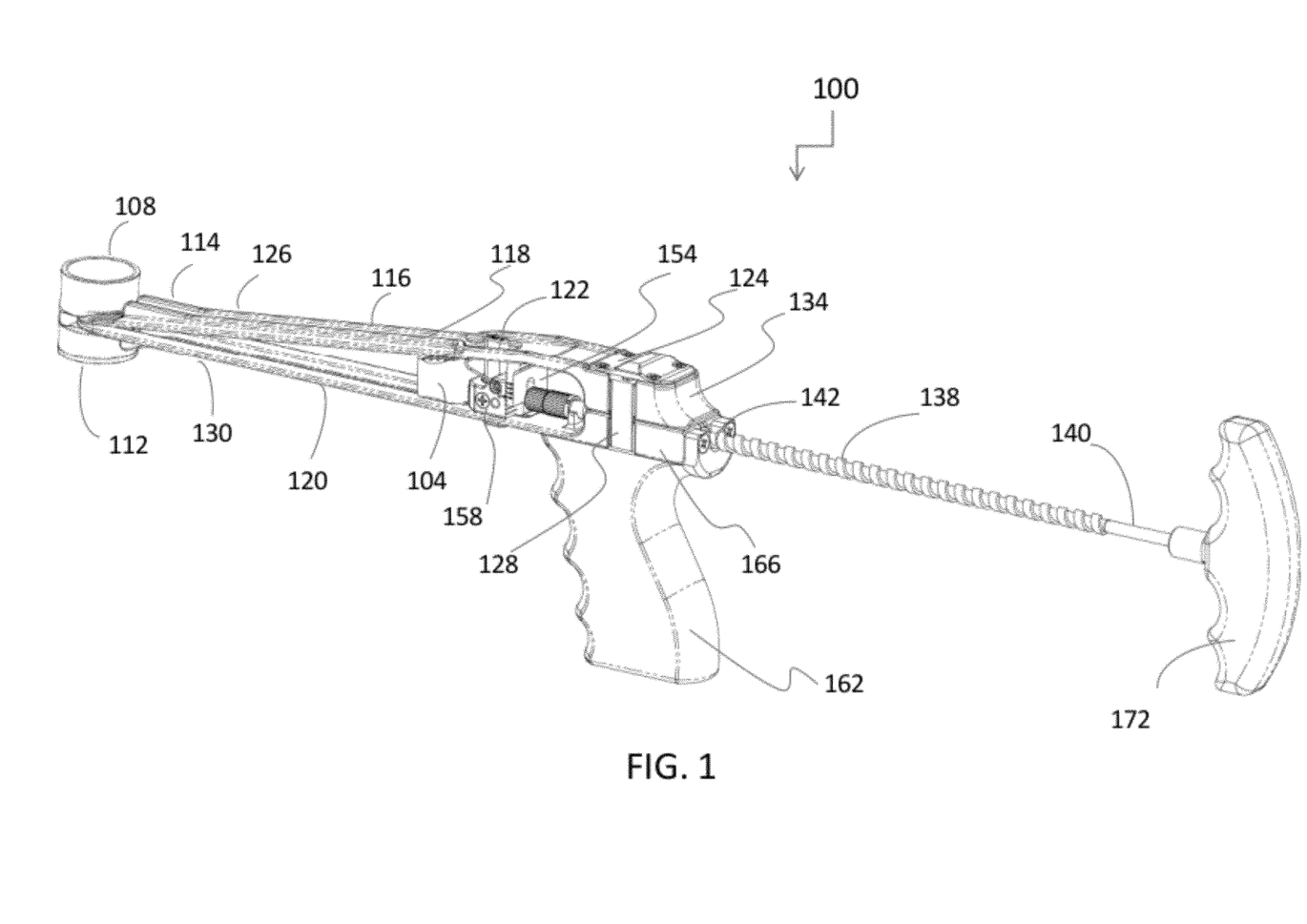
FIGS. 1-4 illustrate an instrument for inserting an implant in an intervertebral space in accordance with one embodiment.

A blade 146 is formed at the distal end 126 of the upper ramp 116, and a blade 150 is formed at the distal end 130 of the lower ramp 120. As shown in FIG. 1, the blades 146, 150 are sized to be inserted in an intervertebral space between the vertebrae 108, 112. Parallel narrow ridges 148, teeth or other uneven structure may be formed on the blades 146, 150 to provide increased friction with the vertebrae 108, 112. The narrow ridges 148 prevent the instrument 100 from dislodging during operation.

In one embodiment, a pair of stop structures 114 project from opposite sides of the channels 118 near the distal ends of the upper and lower ramps 116, 120. As shown in FIG. 1, as the instrument 100 is inserted between the vertebrae 108 and 112, the stop structures 114 prevent the instrument 100 from advancing too far into the intervertebral space, thus preventing damage to the spine.

Figure 3:
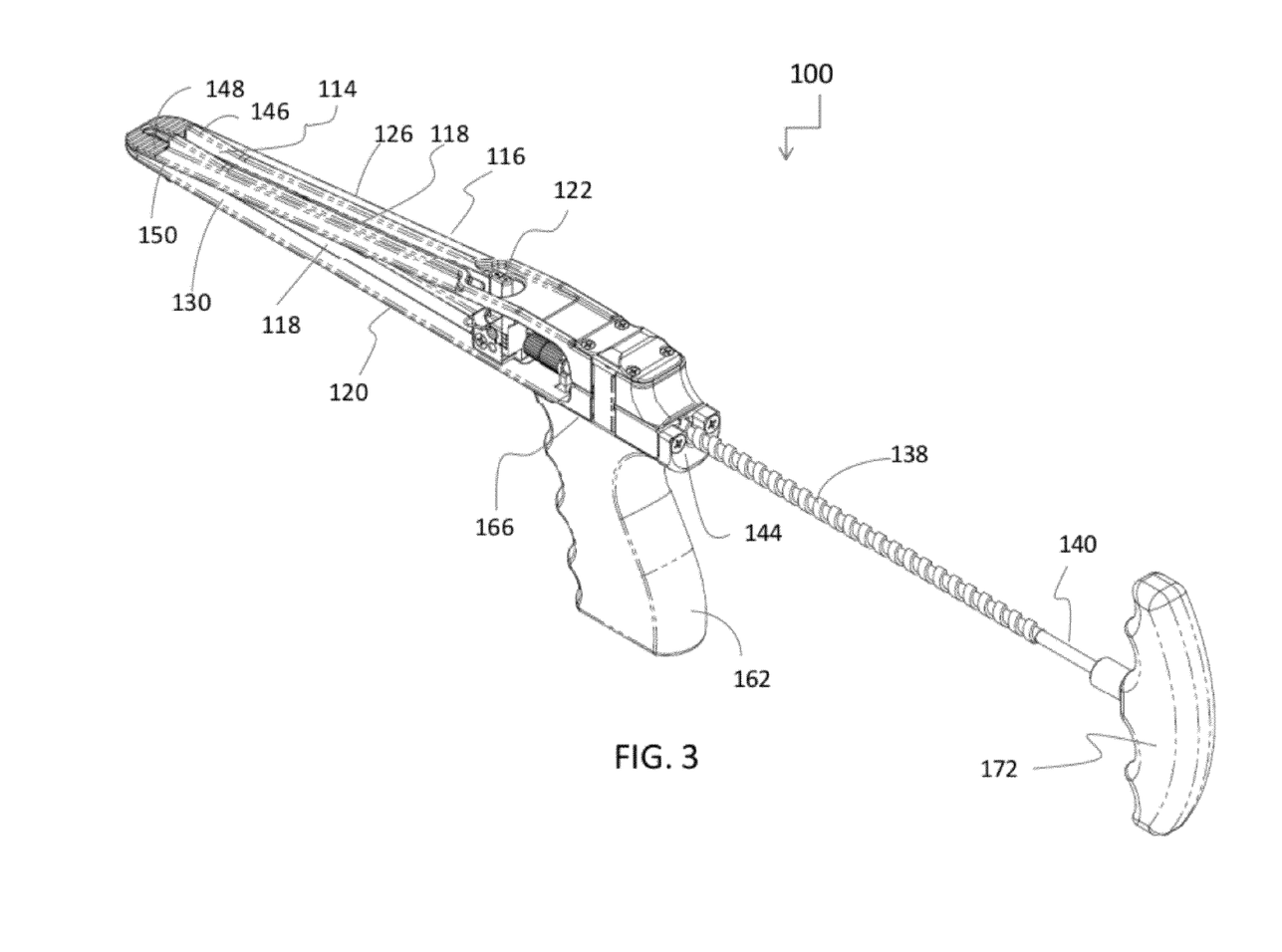
Figure 4:
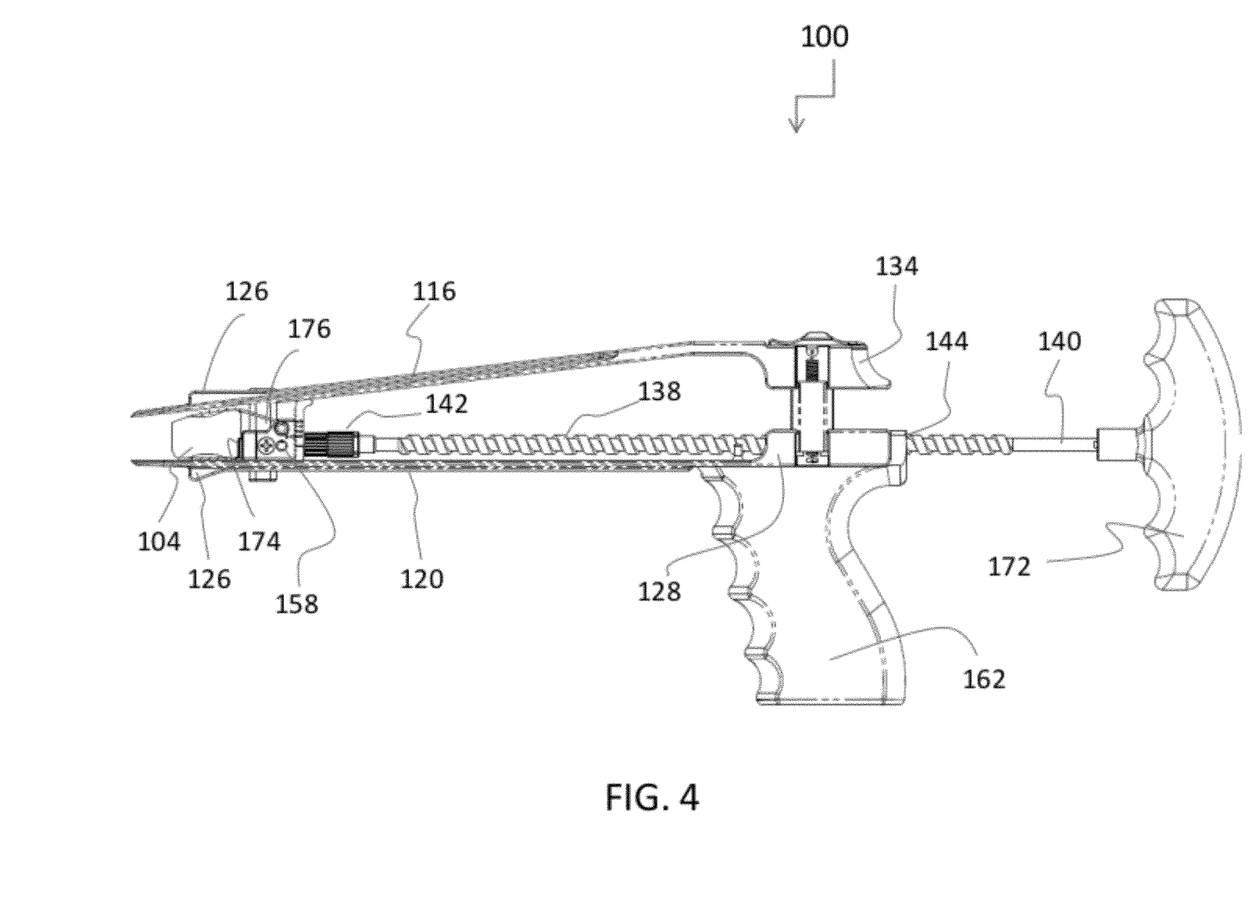

At the proximal ends 124, 128, the upper and lower ramps 116, 120 are coupled to a bracket assembly 134. A grip 162 having a base 166 supports the bracket assembly 134. In a retracted position, as shown in FIGS. 1 and 3, the upper and lower ramps 116, 120 are biased closed at the distal ends 126, 130. The bracket assembly 134 may be spring-loaded or may include other mechanism to bias or tilt the upper and lower ramps 116, 120 closed at the distal ends.

In one embodiment, the bracket assembly 134 and the upper ramp 116 are configured to permit the upper ramp 116 to pivot, or flex, about the bracket assembly 134. The bracket assembly 134 may be spring-biased or may include other means to permit the upper ramp 116 to pivot, or flex, about the bracket assembly 134. However, the lower ramp 120 is rigidly attached to the bracket assembly 166 and does not pivot or flex about the bracket assembly 134. It will be apparent that the opposite arrangement can also be employed so that the upper ramp is rigidly attached while the lower ramp is allowed to pivot or flex. In one embodiment, the bracket assembly 134 self retains the upper ramp 116 and lower ramp 120 in position when the drive member 138 is not forwardly or rearwardly moved (i.e., drive member is stationary). Consequently, the instrument 100 does not require the operator's hands to squeeze the upper and lower ramps 116, 120 together to help maintain closure prior to insertion of the implant.

The instrument 100 includes a drive member 138 having a longitudinal axis. A portion of the drive member 138 has a screw thread thereon. The drive member 138 is disposed between the upper and lower ramps 116, 120 and extends through a correspondingly threaded passage 144 in the bracket assembly 134. The drive member 138 is movable forwardly or rearwardly by applying rotational force to the drive member 138. A handle 172 is attached to a proximal end 140 of the drive member 138. The handle 172 is used to turn and apply rotational force to the drive member 138.

The distal end of the drive member 138 engages an adjustable spreader 154. The adjustable spreader 154 is positioned between the upper and lower ramps 116, 120. In one implementation, the drive member 138 is coupled to the adjustable spreader 154 via a ring 142. The ring 142 receives the drive member 138 and allows the drive member to rotate without applying a rotational force to the ring 142. It will thus be appreciated that the adjustable spreader 154 is movable forwardly or rearwardly by rotating the drive member 138 in relation to the bracket assembly 134.

In one implementation, the adjustable spreader 154 is supported by the lower ramp 120 as the adjustable spreader 154 moves forwardly or rearwardly due to a rotation of the drive member 138. Due to the biasing of the upper ramp 116, the upper ramp 116 bears against the adjustable spreader 154 as the adjustable spreader 154 forwardly advances along the longitudinal axis causing the upper ramp 116 to distract, i.e., separate or move away from the lower ramp 120. The separation or distraction between the upper and lower ramps 116, 120 increases as the adjustable spreader 154 is advanced forwardly toward the distal end of the ramps.

Referring again to FIG. 2, as the drive member 138 pushes the adjustable spreader 154 forwardly, the blades 146, 150 separate and apply a distraction force to the vertebrae 108, 112 to cause them to be distracted sufficiently to receive the implant 104. The drive member 138 is moved forwardly further until the implant is in the intervertebral space.

Figure 2:
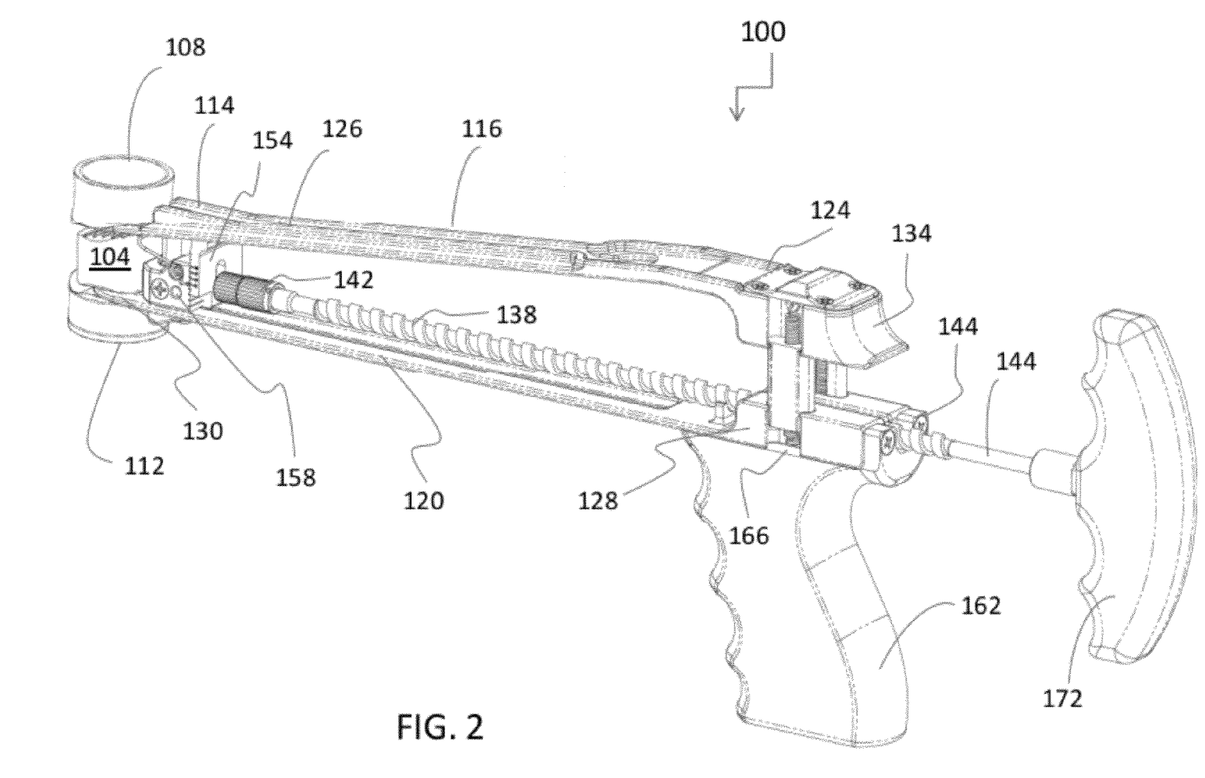

Depending on the height of the implant 104, the adjustable spreader 154 can be calibrated by raising or lowering it in relation to the drive member 138. By raising or lowering the adjustable/calibratible spreader 154, the final distraction of the upper ramp 116 can be varied to create adequate gap between the vertebrae to receive the implant 104. Thus, it will be appreciated that only the upper ramp 116 distracts due to the forwardly movement of the adjustable spreader 154, while the lower ramp 120 remains stationary.

An implant holder 158 is positioned forwardly of the adjustable spreader 154 and is coupled to the adjustable spreader 154. The implant holder 158 is configured to hold the implant 104 during forward and rearward movement along the longitudinal axis. The implant holder 158 inserts the implant between the vertebrae 108, 112 and, as the drive member 138 is moved rearwardly during withdrawal of the instrument 100, the implant holder 158 releases the implant 104 in the intervertebral space between the vertebrae 108, 112.

In one implementation, the implant holder 158 includes a foot 174 for supporting the implant 104 and a spring-biased wire loop 176 for grasping and bearing the implant 104 on the foot 174. Secured between the foot 174 and the wire loop 176, the implant 104 is movable distally or forwardly by manipulating the drive member 138 relative to the bracket assembly 134.

In operation, the implant 104 is secured to the implant holder 158 and fully retracted or withdrawn proximate to the bracket 134. In the fully retracted position, the adjustable spreader 154 is calibrated based on the height of the implant 104. Thereafter, the instrument 100 is inserted between the vertebrae 108, 112, and the drive member 138 is advanced forwardly by rotating the handle 172. As the drive member 138 is advanced forwardly, the upper ramp 116 is distracted by the adjustable spreader 154, which causes distraction force to be applied to the vertebrae 108, 112. The vertebrae 108, 112 are separated sufficiently to receive the implant 104.

After the implant 104 is positioned between the vertebrae 108, 112, the drive member 138 is refracted by rotating the handle 172, causing withdrawal of the distraction force from the vertebrae 108, 112. As a result, the vertebrae 108, 112 exert compressive force on the implant 104 to firmly retain the implant 104 in the intervertebral space. The withdrawal of the drive member 138 also causes the implant holder 158 to release the implant 104. In one embodiment, the spring-biased wire loop 176 releases the implant 104 when the withdrawal force exceeds a predetermined threshold.

During forward and rearward movement, the implant 104 is not in contact with the upper and lower ramps 116, 120. The upper ramp 116 is distracted sufficiently so that the implant 104 is not in contact with the upper ramp 116. The foot 174 of the implant holder 158 maintains a separation between the lower ramp 120 and the implant. Consequently, the implant 104 moves forwardly and rearwardly between the upper and lower ramps 116, 120 without being in contact with the upper and lower ramps 116, 120. Furthermore, as the vertebrae 108, 112 are separated by the upper and lower ramps 116, 120 and the implant 10 is positioned between the vertebrae 108, 112, the implant 104 does not come in contact with the upper and lower ramps 116, 120. By preventing the implant 104 from being in contact with the upper and lower ramps 116, 120, the implant 104 is protected from compressive force or shearing. Also, because the implant moves freely without being in contact with the upper and lower ramps 116, 120, no friction is encountered as the implant moves between the ramps and less force is required to position the implant 104 in the intervertebral space.

Figure 5:
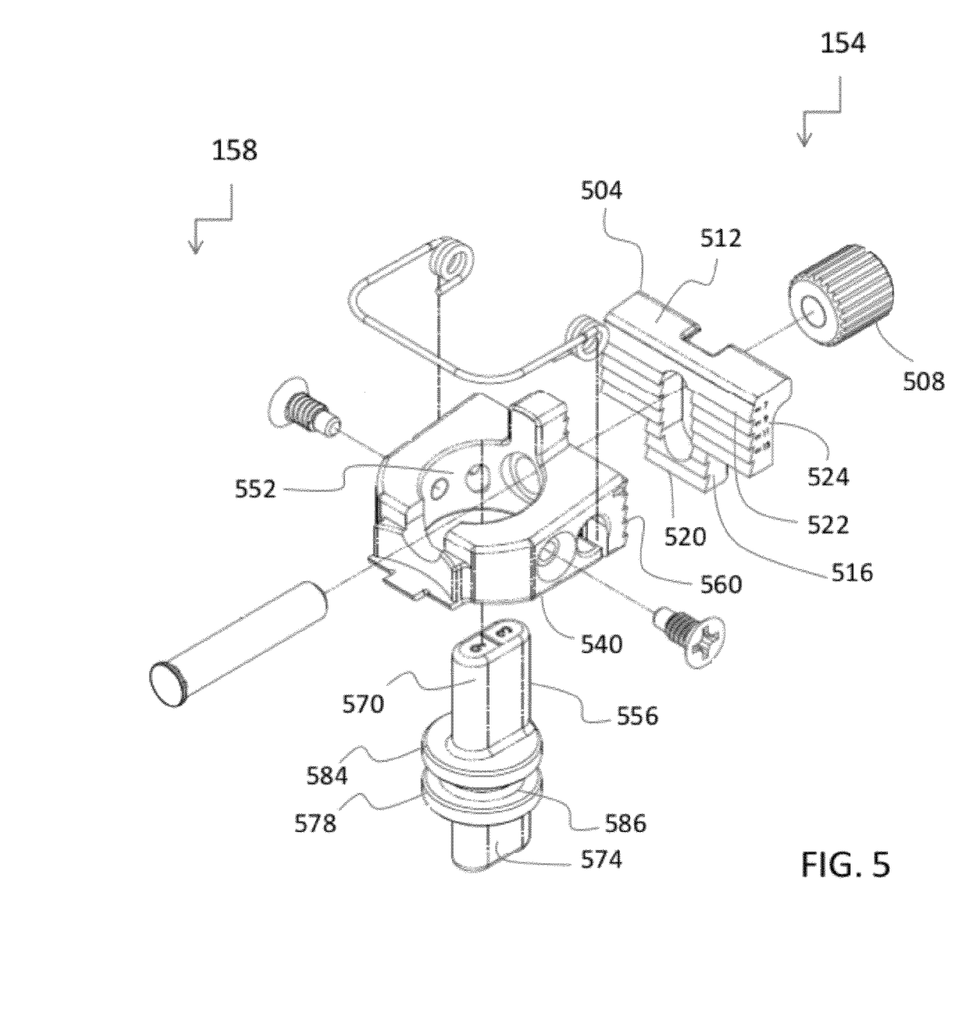
FIG. 5 illustrates components of an adjustable spreader and an implant holder.

FIG. 5 illustrates exploded views of the components of the adjustable spreader 154 and the implant holder 158 in accordance with one embodiment of the invention. The adjustable spreader 154 includes a block 504 having an upper surface 512, a front surface 522 and a rear surface 524. The upper surface 512 supports the upper ramp 116 as the adjustable spreader 154 moves back and forth due to the rotational movement of the drive member 138. Parallel teeth or grooves are formed on the front surface 522 to match with teeth or grooves formed on the rear surface of the implant holder 158. The adjustable spreader 154 includes a rotatable knob 508 that is used to raise or lower the block 504 in relation to the implant holder 158. The matching teeth or grooves on the block 504 and the implant holder 158 jointly maintain or fix the position or elevation of the adjustable spreader 154 in relation to the implant holder 158. By raising or lowering the adjustable spreader 154 in relation to the implant holder 158, the final separation or distraction of the upper ramp 116 relative to the lower ramp 120 is controlled. A lower surface 516 of the block 504 has a projection 520 sized to move freely back and forth within the channel 118 in the lower ramp 120, thus maintaining alignment of the block 504 during forwardly and rearwardly movement and also preventing any rotational movement of the adjustable spreader 154.

Referring again to FIG. 5, the implant holder 158 includes a body 540 having a bore 552 extending centrally. A rod 556 has arms 570 and 574 and a central portion 578 with indentations 584 and a groove 586. The rod 556 may have an elliptical, oval or other suitable cross section. The arms 570, 574 may be off center in relation to the central portion 578.

The rod 556 may be held in the body 540 by screws that engage the indentations 584. When the rod 556 is held in the body 540, the rod 556 is positioned approximately vertical in relation to the upper and lower ramps 116, 120. When the arms 570, 574 are located within the apertures 122, the central portion 578 can be rotated within the bore 552. By rotating the arms 570, 574, they can be positioned closer or farther from the distal ends of the upper and lower ramps 116,120. As a result, the countersink depth of the implant 104 between the vertebrae 108, 112 can be controlled.

Figure 6:
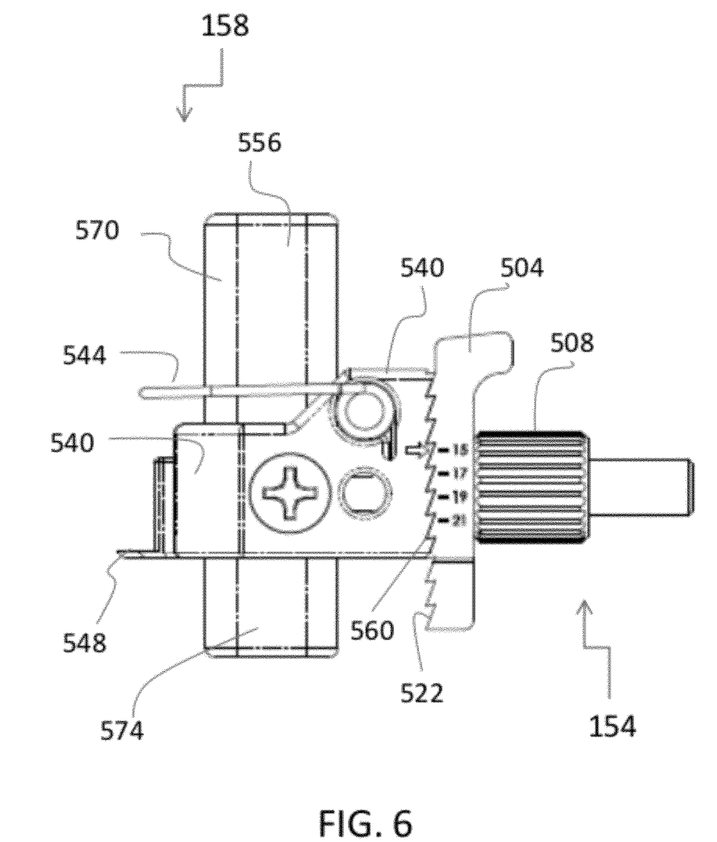
FIG. 6 shows the implant holder coupled to the adjustable spreader.

FIG. 6 shows the implant holder 158 coupled to the adjustable spreader 154. The rotatable knob 508 is used to adjust the elevation of the adjustable spreader 154 in relation to the drive member 138, thus controlling the final distraction of the upper ramp 116. The rod 556 is held in the body 540. The arms 570, 574 may be rotated to control the countersink depth of the implant 104 between the vertebrae.

In one embodiment, a method for inserting an implant between two adjacent vertebrae includes the step of inserting the instrument 100 in an intervertebral space between the vertebrae. The method includes the step of separating the vertebrae by distracting the upper ramp of the instrument while the lower ramp remains stationary. The method includes the step of inserting the implant in the intervertebral space. The method includes the step of retracting the instrument from the intervertebral space wherein the implant is released by the instrument upon retraction.

The components of the instrument 100 may be made from steel, metal alloy or other suitable material. The grip and the handle may be made from plastic, wood or other suitable material.

Having thus described the present invention by reference to certain embodiments, it is noted that the embodiments disclosed are illustrative rather than limiting in nature and that a wide range of variations, modifications, changes, and substitutions are contemplated in the foregoing disclosure and, in some instances, some features of the present invention may be employed without a corresponding use of the other features. Many such variations and modifications may be considered obvious and desirable by those skilled in the art based upon a review of the foregoing description of preferred embodiments. Accordingly, it is appropriate that the appended claims be construed broadly and in a manner consistent with the scope of the invention.

The invention claimed is:

1. An instrument for inserting an implant between vertebrae, comprising:
   an upper and a lower ramp each having a respective proximal and a distal end;
   a bracket assembly coupled to the upper and lower ramps at the proximal ends, the bracket assembly biasing the upper and lower ramps closed at the distal end;
   a drive member having a longitudinal axis and a screw thread thereon, the drive member disposed between the upper and lower ramps and extending through a passage in the bracket assembly;
   an adjustable spreader operably coupled to the drive member and movable between the upper and lower ramps along the longitudinal axis by rotation of the drive member, the upper ramp bearing against the adjustable spreader as the spreader forwardly advances along the longitudinal axis causing the upper ramp to separate from the lower ramp, the extent of distraction being defined by the adjustable spreader; and
   an implant holder coupled to the adjustable spreader, the implant holder comprising a foot for supporting the implant and a spring-biased wire loop for grasping the implant, the implant holder configured to releasably hold the implant during forward advancement along the longitudinal axis, the implant separated from the upper and lower ramps.

2. The instrument as recited in claim 1, wherein the lower ramp is rigidly attached to the bracket assembly and does not pivot about the bracket assembly during forwardly and rearwardly movement of the drive member.

3. The instrument as recited in claim 1, wherein the upper and lower ramps each include a centrally located channel with an aperture near the proximal ends.

4. The instrument as recited in claim 3, wherein the adjustable spreader comprises a block having a projection sized to move freely within the channel in the lower ramp and an upper surface for supporting the upper ramp.

5. The instrument as recited in claim 1, further comprising a vertebral stop projecting proximate the distal end of the upper and lower ramps to limit forward advancement of the ramps inside an intervertebral space.

6. The instrument as recited in claim 1, wherein the implant holder comprises a rod having arms and a central portion for controlling a countersink depth of the implant between the vertebrae.

7. The instrument as recited in claim 1, wherein the adjustable spreader is coupled to the drive member to enable the drive member to rotate without exerting rotational force on the adjustable spreader.

8. The instrument as recited in claim 1, wherein the upper ramp bears against the adjustable spreader during back and forth movement of the adjustable spreader.

9. The instrument as recited in claim 1, wherein the adjustable spreader is adjusted to define the maximum separation of the ramps.

10. The instrument as recited in claim 1, wherein the spring-biased wire loop is configured to release the implant in an intervertebral space when the drive member moves rearwardly.

11. The instrument as recited in claim 1, further comprising a grip having a base to which is attached the bracket assembly.

12. The instrument as recited in claim 1, further comprising a handle coupled to the drive member for applying rotational force to the drive member.

13. The instrument as recited in claim 1, wherein the bracket assembly self retains the upper and the lower ramps in position.

14. An instrument for inserting an implant between vertebrae, comprising:
   an upper and a lower ramp each having a respective proximal and a distal end, the upper and lower ramps each including a centrally located channel with an aperture near the proximal ends;
   a bracket assembly coupled to the upper and lower ramps at the proximal ends, the bracket assembly biasing the upper and lower ramps closed at the distal end, the lower ramp being rigidly attached to the bracket assembly, the lower ramp not pivoting about the bracket assembly;
   a threaded drive member disposed between the upper and lower ramps and extending through a passage in the bracket assembly;
   an adjustable spreader operably coupled to the drive member and movable between the upper and lower ramps along the longitudinal axis by rotation of the drive member, the adjustable spreader having an upper surface for supporting the upper ramp and a projection sized to move freely within the channel in the lower ramp, the adjustable spreader separating the upper ramp from the lower ramp during forwardly movement; and an implant holder coupled to the adjustable spreader, the implant holder having a seat for supporting the implant and a spring-biased wire loop for releasably retaining the implant, the implant not being in contact with the upper and lower ramps during back and forth movement of the implant.

15. The instrument as recited in claim 14, further comprising a vertebral stop projecting proximate the distal end of the upper and lower ramps to limit forward advancement of the ramps inside an intervertebral space.

16. The instrument as recited in claim 14, wherein the implant holder comprises a rod having arms and a central portion for controlling the countersink depth of the implant between the vertebrae.

17. The instrument as recited in claim 14, wherein the adjustable spreader is coupled to the drive member to enable the drive member to rotate without exerting rotational force on the adjustable spreader.

18. The instrument as recited in claim 14, wherein the upper ramp bears against the adjustable spreader during back and forth movement of the adjustable spreader.

19. The instrument as recited in claim 14, wherein the adjustable spreader is adjusted to define a maximum distraction of the upper ramp.

20. The instrument as recited in claim 14, wherein the spring-biased wire loop is configured to release the implant in an intervertebral space when the drive member is moved rearwardly.

21. The instrument as recited in claim 14, further comprising a grip having a base to which is attached the bracket assembly.

22. The instrument as recited in claim 14, further comprising a handle operably coupled to the drive member for applying rotational force to the drive member.

23. An instrument for inserting an implant between vertebrae, comprising:
    an upper and a lower ramp having a respective proximal and a distal end, the distal ends having a respective blade sized to be inserted into an intervertebral space;
    a bracket assembly coupled to the upper and lower ramps at the proximal ends, the bracket assembly biasing the upper and lower ramps closed at the distal end;
    a drive member having a longitudinal axis and a screw thread thereon, the drive member disposed between the upper and lower ramps and extending through a passage in the bracket assembly;
    an adjustable spreader operably coupled to the drive member and movable between the upper and lower ramps along the longitudinal axis by rotational motion of the drive member, the elevation of the adjustable spreader being adjustable in relation to the drive member to control the distraction of the upper ramp, the adjustable spreader having an upper surface for supporting the upper ramp and a projection sized to move freely within a channel in the lower ramp, the adjustable spreader distracting the upper ramp during forwardly movement along the longitudinal axis while the lower ramp remains stationary; and
    an implant holder coupled to the adjustable spreader, the implant holder having a seat for supporting the implant and a spring-biased wire loop for grasping the implant, the implant not being in contact with the upper and lower ramps during back and forth movement along the longitudinal axis.

24. The instrument as recited in claim 23, further comprising a vertebral stop projecting proximate the distal end of the upper and lower ramps to limit forward advancement of the ramps inside an intervertebral space.

25. The instrument as recited in claim 23, wherein the implant holder comprises a rod having arms and a central portion for controlling the countersink depth of the implant between the vertebrae.

26. The instrument as recited in claim 23, wherein the adjustable spreader is freewheelingly coupled to the drive member to enable the drive member to rotate without exerting rotational force on the adjustable spreader.

27. The instrument as recited in claim 23, wherein the adjustable spreader is calibrated to limit maximum distraction of the upper ramp.

28. The instrument as recited in claim 23, wherein the spring-biased wire loop is configured to release the implant in an intervertebral space when the drive member is moved rearwardly.

29. The instrument as recited in claim 23, further comprising a grip having a base to which is attached the bracket assembly.

30. The instrument as recited in claim 23, further comprising a handle operably coupled to the drive member for applying rotational force to the drive member.

* * * * *